United States Patent
Zhao et al.

(10) Patent No.: US 11,607,462 B2
(45) Date of Patent: Mar. 21, 2023

(54) SYSTEMS AND METHODS FOR MINIMALLY-INVASIVE ASSESSMENT OF TOXICITY-INDUCED TISSUE INJURY

(71) Applicant: Northwestern University, Evanston, IL (US)

(72) Inventors: Ming Zhao, Wilmette, IL (US); Steven E. Johnson, Milwaukee, WI (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/981,568

(22) Filed: May 16, 2018

(65) Prior Publication Data

US 2018/0333506 A1  Nov. 22, 2018

Related U.S. Application Data

(60) Provisional application No. 62/506,903, filed on May 16, 2017.

(51) Int. Cl.

| | | |
|---|---|---|
| A61K 51/00 | (2006.01) | |
| A61M 36/14 | (2006.01) | |
| A61K 49/00 | (2006.01) | |
| A61K 51/04 | (2006.01) | |
| A61K 51/08 | (2006.01) | |
| A61K 49/06 | (2006.01) | |
| G01N 33/50 | (2006.01) | |

(52) U.S. Cl.
CPC ...... *A61K 49/0002* (2013.01); *A61K 51/0474* (2013.01); *A61K 51/08* (2013.01); *A61K 51/088* (2013.01); *A61K 49/06* (2013.01); *A61K 2123/00* (2013.01); *G01N 33/5091* (2013.01); *G01N 2510/00* (2013.01)

(58) Field of Classification Search
CPC ............ A61K 49/0002; A61K 51/0474; A61K 51/08; A61K 51/088; A61K 49/06; A61K 2123/00; G01N 33/5091; G01N 2510/00
See application file for complete search history.

(56) References Cited

U.S. PATENT DOCUMENTS

| | | | |
|---|---|---|---|
| 4,657,659 A | 4/1987 | Mase et al. | |
| 4,885,363 A | 12/1989 | Tweedle et al. | |
| 5,087,440 A | 2/1992 | Cacheris et al. | |
| 5,155,215 A | 10/1992 | Ranney | |
| 5,188,816 A | 2/1993 | Sherry et al. | |
| 5,219,553 A | 6/1993 | Kraft et al. | |
| 5,262,532 A | 11/1993 | Tweedle et al. | |
| 5,358,704 A | 10/1994 | Desreux et al. | |
| 7,511,124 B2 * | 3/2009 | Thorpe | A61K 39/395 530/402 |
| 2003/0003048 A1 * | 1/2003 | Li et al. | A61K 51/00 424/1.49 |

OTHER PUBLICATIONS

Johnson et al. (J. Nucl. Med. 2013, 54, 1397-1403).*
Elves et al. (Mol. Imaging Biol. 2015, 17, 838-847).*
Fujita et al. (World J Gastroenterol Nov. 21, 2015; 21(43): 12234-12248).*
Elvas et al. (J. Nucl. Med. 2016, 57, 805-811).*
Torrisi et al. (Radiology 2011, 258, 41-56).*
D. Meyers et al., "Advances in Macrocyclic Gadolinium Complexes as Magnetic Resonance Imaging Contrast Agents", Invest Radiol. 1990, 25: S53-55.
Kapty et al., "Evaluation of phosphatidylserine-binding peptides targeting apoptotic cells", J. Biomol Screen. Dec. 2012; 17(10): 1293-301.
Igarashi et al., "A Novel Phosphatidylserine-binding Peptide Motif Defined by an Anti-idiotypic Monoclonal Antibody", J. Biol Chem. Dec. 8, 1995: 270(49) 29075-8.
Sao et al., "How chemotherapy and radiotherapy damage the tissue: Comparative biology lessons from feather and hair models", Experimental Dermatology, 2019; 28:413-418.

* cited by examiner

*Primary Examiner* — Michael G. Hartley
*Assistant Examiner* — Melissa J Perreira
(74) *Attorney, Agent, or Firm* — Benesch, Friedlander, Coplan & Aronoff LLP

(57) ABSTRACT

Provided herein are compositions, systems, and methods for minimally-invasive assessment of toxicity-induced tissue injury. In particular, external (e.g., whole-body) scanning is employed to detect toxicity-induced injuries, such as those caused by chemotherapeutics.

3 Claims, 12 Drawing Sheets

SYSTEMS AND METHODS FOR MINIMALLY-INVASIVE ASSESSMENT OF TOXICITY-INDUCED TISSUE INJURY

CROSS-REFERENCE TO RELATED APPLICATION

The present application claims priority to U.S. Provisional Patent Application Ser. No. 62/506,903 filed May 16, 2017, which is herein incorporated by reference in its entirety.

FIELD

Provided herein are compositions, systems, and methods for minimally-invasive assessment of toxicity-induced tissue injury. In particular, external (e.g., whole-body) scanning is employed to detect toxicity-induced injuries, such as those caused by chemotherapeutics.

BACKGROUND

Chemotherapeutics are a class of drugs known for their cytotoxic qualities against cancerous growth, but their efficacy is often limited by collateral tissue damage. Conventional preclinical toxicology studies rely heavily on histopathological analyses using excised tissues. However, notable drawbacks for toxicity studies are that complete histopathological evaluations tend to be cumbersome, time intensive and costly. In addition, histopathology may be prone to sampling errors when toxicity responses are spatially heterogeneous. When the observation of significant toxicity is made at a relatively late stage in the process of drug discovery, it may lead to the termination of a particular lead and occasionally an entire program, resulting in substantial loss of time and financial resources. This can be an important barrier to drug discovery when there are multiple pharmacophores that need to be prioritized for further optimization. More recently, drug discoverers have come to appreciate the need to conduct toxicology early in order to identify problematic pharmacophores. While there has been a rapid expansion of in vitro and cell-based toxicity assays, there lacks methodologies for minimally invasive, systemic evaluation of toxicities in vivo at an organismal level.

SUMMARY

Provided herein are compositions, systems, and methods for minimally-invasive assessment of toxicity-induced tissue injury. In particular, external (e.g., whole-body) scanning is employed to detect toxicity-induced injuries, such as those caused by chemotherapeutics. In some embodiments, provided herein are methods of assessing toxicity-induced tissue injury in a subject comprising: (a) administering a molecular imaging agent to the subject, wherein the molecular imaging agent comprises (i) a detectable moiety and (ii) a binding moiety that binds to a marker of toxicity-induced tissue injury; (b) performing a molecular imaging scan of the subject; and (c) detecting the marker of toxicity-induced tissue injury within the subject. In some embodiments, the detectable moiety comprises a metal ion, stable isotope, or radionuclide. In some embodiments, the molecular imaging agent comprises a chelating moiety coordinated to a metal ion, stable isotope, or radionuclide. In some embodiments, the ion, stable isotope, or radionuclide is selected from technetium-99m ($^{99m}Tc$), gallium-67 ($^{67}Ga$), yttrium-91 ($^{91}Y$), indium-111 ($^{111}In$) rhenium-186 ($^{186}Re$), thallium-201 ($^{201}Tl$), gadolinium(III), iron oxide, iron platinum, and manganese. In some embodiments, the binding moiety is capable of binding to a marker of apoptosis and/or necrosis. In some embodiments, the binding moiety binds to externalized phospholipid. In some embodiments, the binding moiety binds to phosphatidylethanolamine (PE). In some embodiments, the binding moiety comprises a lanthionine-containing peptide antibiotic or a PE-binding portion thereof. In some embodiments, the binding moiety is selected from duramycin, duramycin B, duramycin C, cinnamycin, or a PE-binding portion thereof. In some embodiments, the binding moiety binds to phosphatidylserine (PS). In some embodiments, the binding moiety comprises a PS-binding peptide. In some embodiments, the molecular imaging agent is $^{99m}Tc$-duramycin.

In some embodiments, the molecular imaging scan comprises a technique selected from Magnetic Resonance Imaging (MRI), planar scintigraphy (PS), Positron Emission Tomography (PET), Single Photon Emission Computed Tomography (SPECT), and Computed Tomography (CT). In some embodiments, the molecular imaging scan comprises a whole body scan. In some embodiments, the molecular imaging scan is non-invasive.

In some embodiments, methods herein are performed following exposure of the subject to a potentially toxic agent or condition. In some embodiments, methods herein are performed following exposure of the subject to a chemotherapeutic or other potentially toxic drug. In some embodiments, the subject is a human and the method is performed to assess toxicity-induced injury to the subject from the potentially toxic agent or condition. In some embodiments, the subject is a non-human animal (e.g., primate, rodent, canine, etc.) and the method is performed to assess the toxicity of the potentially toxic agent or condition to future subjects.

In some embodiments, provided herein are methods of assessing toxicity-induced tissue injury in a subject comprising: (a) administering a bioactive agent to a subject; (b) performing a molecular imaging scan of the subject; and (c) detecting changes related to toxicity-induced tissue injury from the bioactive agent. In some embodiments, the molecular imaging scan comprises a technique selected from Magnetic Resonance Imaging (MRI), planar scintigraphy (PS), Positron Emission Tomography (PET), Single Photon Emission Computed Tomography (SPECT), and Computed Tomography (CT). In some embodiments, the molecular imaging scan comprises a whole body scan. In some embodiments, methods further comprise administering to the subject an imaging agent. In some embodiments, the imaging agent is an apoptosis and/or necrosis imaging agent. In some embodiments, the imaging agent is a detectable phosphatidylethanolamine (PE)-specific agent. In some embodiments, the imaging agent comprises duramycin. In some embodiments, the imaging agent is $^{99m}Tc$-duramycin. In some embodiments, the imaging agent comprises a paramagnetic metal ion and/or a radionuclide. In some embodiments, the bioactive agent is a chemotherapeutic.

DETAILED DESCRIPTION

Provided herein are compositions, systems, and methods for minimally-invasive assessment of toxicity-induced tissue injury. In particular, external (e.g., whole-body) scanning is employed to detect toxicity-induced injuries, such as those caused by chemotherapeutics.

Pathologically elevated cell death, in the forms of apoptosis and necrosis, is an important manifestation of terminal cellular response in toxicity-induced tissue injuries. Compared to stress-based responses and metabolic changes, a propensity for increased cell death provides an unambiguous marker for the susceptibility of tissues to toxic side effects of a drug. As such, provided herein are systems and methods for external (e.g., whole-body), noninvasive imaging of cell death in order to assess drug toxicity in a systemic, near-real time manner.

Experiments conducted during development of embodiments herein demonstrate that systemic tissue injury, detected through imaging of tumor apoptosis after cancer treatment, is a tangible sign of toxicity-induced tissue injury. Apart from changes in signals in the responding tumor, it was observed that there was an elevation in the systemic "background" after chemotherapy. Experiments were conducted during development of embodiments herein to determine whether these changes in apoptosis imaging were random noise or real reproducible signals that reflect collateral tissue damages as a result of anticancer treatment. $^{99m}$Tc-duramycin was employed as a phosphatidylethanolamine (PE)-specific radiopharmaceutical for detecting signals from systemic tissue injuries. PE is a major constituent at the inner leaflet of the plasma membrane and becomes accessible when a cell loses viability. PE serves as a marker for allowing the noninvasive detection apoptosis and necrosis regardless of the mode of cell death. Duramycin is a polypeptide that has a stereospecific binding pocket for PE. As an imaging agent, $^{99m}$Tc-duramycin has reasonably high target uptake with relatively fast clearance kinetics.

Figure 1:
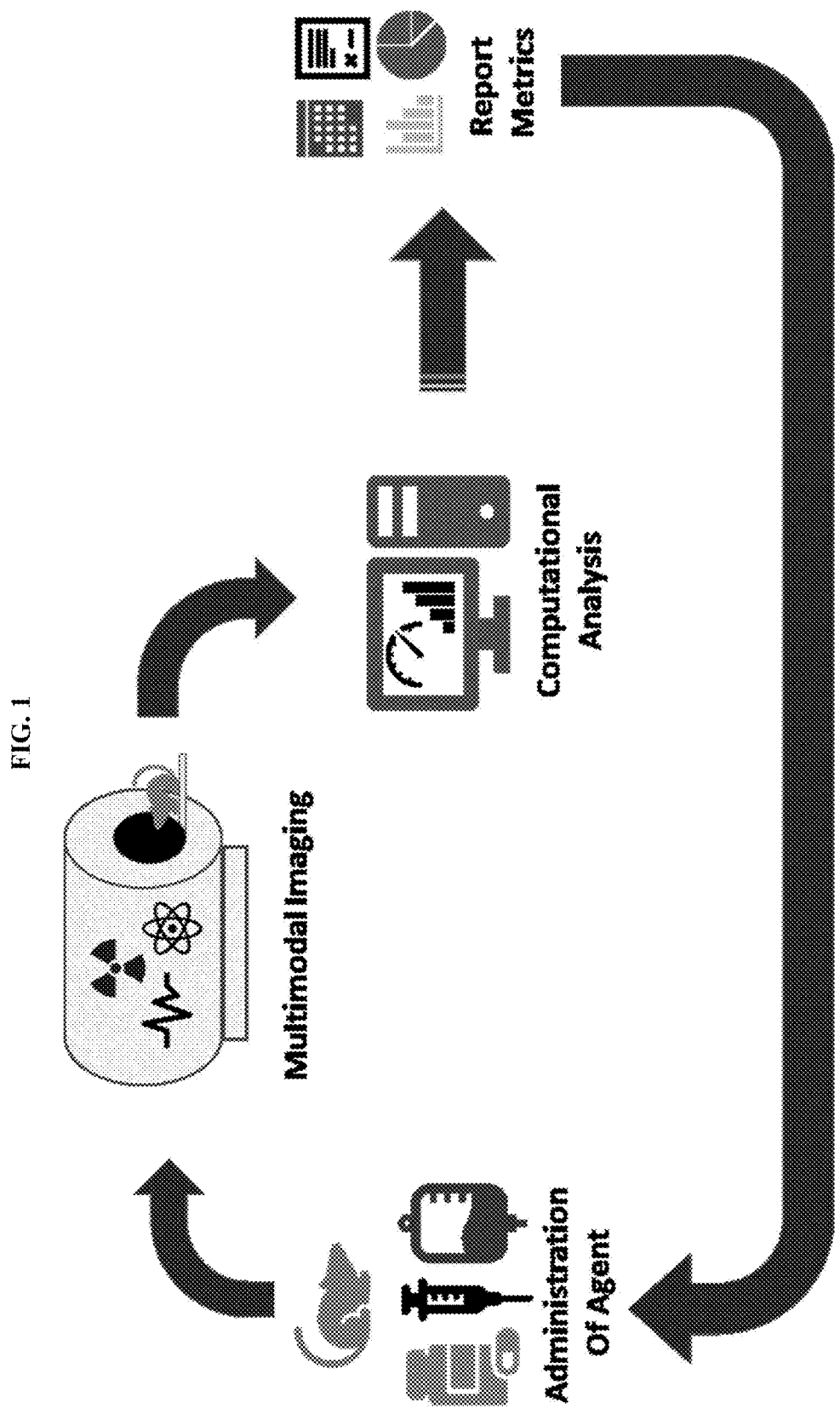
FIG. 1. Schematic diagram of Toxicity Scan.

Experiments conducted during development of embodiments herein demonstrate the use of a toxicity scan (e.g., whole-body scan) for detecting tissue injuries in a minimally invasive, systematic and dynamic fashion. A schematic diagram of an exemplary approach is illustrated in FIG. 1. In some embodiments, signal changes detected by toxicity scan reflect the systemic toxicity profile of an anticancer drug. Experiments were conducted during development of embodiments herein using a rat model, treated with clinically established anticancer drugs with known toxicity profiles, including cyclophosphamide, methotrexate and cisplatin. The drugs were selected for their distinct mechanisms of action and toxicity profiles—cyclophosphamide is an alkylating agent that covalently modifies DNA; methotrexate primarily inhibits dihydrofolate reductase; and cisplatin interferes with DNA replication by forming intra-strand crosslink adducts. Experiments were conducted in multiple phases, by first investigating the feasibility of detecting a signal change using quantitative ex vivo study, followed by single-time point imaging studies which were cross-validated using histopathological analyses and compared to serum and metabolic panels. The utility for noninvasive toxicity profiling was examined for delineating the spatiotemporal kinetics of adverse toxicity effects in a multi-time point dynamic study. Experiments described herein represent the first investigation to explore the novel approach for characterizing drug toxicity-induced tissue injury systemically, dynamically and in near-real time. In some embodiments, the systems and methods described herein provide useful tools in drug research and development, particularly in the earlier phase of pharmacological assessment. In other embodiments, particularly given the minimally invasive nature of the systems and methods herein, approached herein are useful for assessing toxicity in patients, for example, in an individualized fashion for personalized care with precision medicine.

In some embodiments, provided herein are systems and methods for noninvasive imaging approach for assessing tissue injuries induced by drug toxicity. The signal changes detected by a toxicity scan reflect the systemic toxicity profile of a chemotoxic drug. Pharmaceuticals vary in toxicity and therapeutic efficacy as a consequence of mechanisms of action, pharmacodynamics and pharmacokinetic properties. A minimally invasive approach for detecting adverse effects on an individualized basis provides value in determining the toxicity profile for a drug or drug candidate. The exemplary chemotherapeutic drugs used in studies herein induce apoptosis of cells in which $^{99m}$Tc-duramycin uptake occurs. A variety of adverse events arise in patients and in animal models upon administration of these compounds. Experiments conducted during development of embodiments herein demonstrate that toxicity profiling by in vivo imaging is consistent with known toxicity from three established chemotherapeutic drugs with distinct toxicity profiles. The findings were supported by comparison to canonical toxicological methods including blood paneling and histopathology.

Drug toxicity can be projected with a broad range of manifestations, from molecular interactions, signaling and metabolic changes to tissue/organismal-level responses such as hormonal and functional dysregulations. Among these, cell death presents a form of terminal and extreme cellular response to toxicity. A significantly elevated level of pathological cell death in a target tissue confers an unambiguous indicator for the susceptibility to the adverse effect of a given drug or treatment. In toxicity assessment, the presence of aggravated cell death raises concern on a drug candidate, and the information contributes unequivocally to the decision making process.

Systemic toxicity is a dynamic individualized occurrence, where tissue response differs spatially and temporally, and each individual may have a different level of susceptibility. The toxicity scan delineates adverse effect-induced tissue injury in a systemic approach. The minimally-invasive (e.g., noninvasive) nature allows repeated scans of the same subject both before and after drug treatment at multiple time points. The in vivo dynamic data detected variations in the onset and progression of signal changes in different organs and tissues. The imaging data provided a visual map (e.g., in a whole body fashion), and are particularly useful for identifying problematic sites when changes are regional and heterogeneous. In addition to the spatial heterogeneity within an organ, there are variations in the same tissue among different individuals. Tissues which exhibit the greatest variations in response to drug toxicity from one individual to another are likely contributors to personalized susceptibility. In this respect, the current studies demonstrated a useful approach for delineating the dynamics of tissue injury in a personalized fashion. Compared to histopathology-based toxicity studies, which necessitate euthanizing multiple groups of animals for full tissue biopsy, the toxicity scan provides indications for susceptible tissues in a continuous fashion in near-real time. The prompt availability of such information is complementary to histopathology-based toxicity studies and accelerates the decision making process in drug discovery and development. The toxicity scan is also applicable to assessing adverse side effects in other therapeutic drugs beyond chemotoxic oncologic pharmaceuticals.

Noninvasive imaging of cell death requires minimizing systemic background and improving target-to-background ratio in order to make it technologically feasible to detect subtle signal changes that reflect the underlying pathology. The use of $^{99m}$Tc-duramycin achieved an appreciable level of sensitivity with a reasonable dynamic range which, to an extent, covers both relatively high and low level signal changes. While the molecular mechanism of phospholipid externalization does not differentiate apoptosis from necrosis, being able to detect a marker for tissue injury regardless of the modes or causes of cell death is a desirable outcome.

In some embodiments, methods and systems herein comprise administering to a subject a molecular imaging agent comprising a detectable moiety. In some embodiments, the subject subsequently undergoes molecular imaging, and characteristics of the subject and/or the molecular imaging agent within the subject (e.g., intensity, distribution, change over time, etc.) is detected/monitored/characterized.

The term "detectable moiety", as used herein refers to any entity which, when part of a molecule, allows visualization of the molecule by using molecular imaging techniques. In the context of the present invention, detectable moieties are entities that are detectable by molecular imaging techniques such as Magnetic Resonance Imaging (MRI), planar scintigraphy (PS), Positron Emission Tomography (PET), Single Photon Emission Computed Tomography (SPECT), or any combination of these techniques. Preferably, detectable moieties are stable, non-toxic entities.

In certain embodiments, a molecular imaging agent is detectable by a nuclear medicine molecular imaging techniques such as planar scintigraphy (PS), Positron Emission Tomography (PET) and Single Photon Emission Computed Tomography (SPECT).

SPECT and PET acquire information on the concentration of radionuclides introduced into a subject's body. PET generates images by detecting pairs of gamma rays emitted indirectly by a positron-emitting radionuclide. A PET analysis results in a series of thin slice images of the body over the region of interest (e.g., brain, breast, liver, whole body, etc.). These thin slice images can be assembled into a three dimensional representation of the examined area. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Planar scintigraphy (PS) is similar to SPECT in that it uses the same radionuclides. However, PS only generates 2D-information.

In certain embodiments, a detectable moiety in a molecular imaging agent is a radionuclide detectable by PET (e.g., Gallium-68 ($^{68}$Ga)). In other embodiments, the detectable moiety is a radionuclide detectable by planar scintigraphy or SPECT. Examples of such radionuclides include technetium-99m ($^{99m}$Tc), gallium-67 ($^{67}$Ga), yttrium-91 ($^{91}$Y), indium-111 ($^{111}$In) rhenium-186 ($^{186}$Re) and thallium-201 ($^{201}$Tl). In some embodiments, the radionuclide is technetium-99m ($^{99m}$Tc).

In certain embodiments, a molecular imaging agent is designed to be detectable by Magnetic Resonance Imaging (MRI). MRI has the advantage of not relying on ionizing radiation. Thus, in certain embodiments, the molecular imaging agent comprises a paramagnetic metal ion. Example of paramagnetic metal ions detectable by MRI is gadolinium III ($Gd^{3+}$), which is an FDA-approved contrast agent for MRI, or iron oxide, which gives a sensitive negative signal in MRI.

In some embodiments, a molecular imaging agent comprises metal-chelating moieties (e.g., for the complexation of paramagnetic metal ions or radionuclides). Such, metal-chelating moieties include DTPA (diethylene triaminepentaacetic acid); DOTA (1,4,7,10-tetraazacyclododecane-N,N',N'',N'''-tetraacetic acid); and derivatives thereof (see, for example, U.S. Pat. Nos. 4,885,363; 5,087,440; 5,155,215; 5,188,816; 5,219,553; 5,262,532; and 5,358,704; and D. Meyer et al., Invest. Radiol. 1990, 25: S53-55), in particular, DTPA-bis(amide) derivatives (U.S. Pat. No. 4,687,659). Other ligands also include NOTA (1,4,7-triaza-cyclononane N,N',N''-triacetic acid), and HYNIC (6-Hydrazinopyridine-3-carboxylic acid).

In some embodiments, a molecular imaging agent that finds use in embodiments herein binds to a marker of toxicity induced injury. In some embodiments, a molecular imaging agent that finds use in embodiments herein binds to a marker of apoptosis and/or necrosis. In some embodiments, a molecular imaging agent that finds use in embodiments herein binds to a marker of both apoptosis and necrosis. In some embodiments, a molecular imaging agent that finds use in embodiments herein binds to a marker that differentiates between apoptosis and necrosis.

Phosphatidylethanolamine (PE) and phosphatidylserine (PS) become externalized during apoptosis and/or necrosis. Therefore, in some embodiments, an agent capable of binding to the externalized PE and/or PS, as well as being detectable by an external (e.g., whole body) scan, finds use in embodiments herein as a molecular imaging agent. Experiments conducted during development of embodiments herein demonstrate the utility of detection of externalized cell membrane phospholipids in the assessment of apoptosis/necrosis and toxicity-induced tissue injury. In particular, a detectable agent comprising duramycin finds use as a molecular imaging agent in some embodiments herein.

In some embodiments, a molecular imaging agent comprises a detectable moiety (e.g., a radionuclide, a chelated radionuclide, etc.) and a PE-binding moiety. In some embodiments, the PE binding moiety is a lanthionine-containing peptide antibiotic, such as, duramycin, duramycin B, duramycin C, cinnamycin, etc.

In some embodiments, a molecular imaging agent comprises a detectable moiety (e.g., a a metal ion, a chelated metal ion, a radionuclide, a chelated radionuclide, a stable isotope, a chelated stable isotope, etc.) and a PS-binding moiety (e.g., a PS-binding peptide (Kapty et al. J Biomol Screen. 2012 December; 17(10):1293-301; Igarashi et al. J Biol Chem. 1995 Dec. 8; 270(49):29075-8; herein incorporated by reference in their entireties), etc.).

In some embodiments, a toxicity scan finds use in toxicity studies, which rely on histopathology-based tissue analyses. An effective way to noninvasively identify injury in intact organs and tissues provides useful indicators that independently validate histopathology findings, particularly when the toxicity effect is heterogeneous and tends to lead to sampling errors in tissue retrieval.

In some embodiments, a toxicity scan finds use in in vivo toxicity assessment in the pharmacology phase of drug development, which is relatively early in drug discovery with the identification of a number of lead candidates. This phase is too early for full-scale toxicity studies for these candidates, yet timely characterizations are essential to reaching a go-no-go decision for the candidates. Given the minimally invasive nature of the in vivo approach, it provides the needed information at near-real time. This information on the spatiotemporal occurrence of adverse effects will help select efficacious drug candidates with lower toxicity for prioritization, while eliminating candidates that are too toxic to vital organs/tissues. The ability to prioritize candidates at the pharmacology phase will help terminate problematic drug candidates early on so that resources can be better focused on bringing the right program forward.

In some embodiments, a toxicity scan finds use in pharmacovigilance. Drugs with unforeseen side effects may need to be reassessed for safety. An in vivo dynamic study in a systematic fashion can be useful for identifying problematic side effects and for testing alternative dosing/formulation to mitigate the issue. In some embodiments, the methods and systems herein find use in, for example: determining drug toxicity-induced tissue damage in an in vivo, whole body, dynamic, noninvasive and/or individualized fashion; pharmacological characterization of drug candidates for eliminating toxic compounds and prioritizing safe, efficacious candidates in preclinical drug R&D; toxicity studies for validating conventional, histopathology-based findings; pharmacovigilence for post-marketing commercial drug products; drug trials in clinical settings to determine toxic side effects in test subjects and corroborate with symptoms; determining susceptibility to drug toxicity in individual patients for personalized treatments; testing for dosing and routes of administration for drugs; detecting heterogeneity in drug response among a population; assessing cardiotoxicity in a multi-organ, multi-parametric approach; assessing the efficacy and side effects of single drugs, drug-drug interactions, and combination therapies; predicting the consistency and/or precariousness of response among a population; assessing toxicity response among homologues and non-homologues tissues; detecting tissues which share common toxicity profiles that are indicative of common underlying mechanisms of drug uptake, retention, metabolism and susceptibility; etc.

The experiments conducted during development of embodiments herein demonstrate the feasibility of the methods and systems herein to characterize toxicity-induced tissue injury. A toxicity scan provides a wealth of information on both individual- and population-levels for gauging systemic tissue injury induced by chemotherapeutics, and has applications in pharmaceutical development, drug discovery, and clinical oncology.

Embodiments herein find use in minimally-invasive detection of necrosis and/or apoptosis in a subject. Particular embodiments herein utilize detection of necrosis and/or apoptosis to access toxicity-induced tissue injury. These embodiments are described herein for the assessment of toxicity of drugs, such as chemotherapeutic agents; however, embodiments herein are not so limited. For example, in some embodiments, the methods and compositions described herein find use in the assessment of toxicity caused by non-chemotherapeutic and/or non-drug agents. In some embodiments, methods herein find use in assessing tissue injury caused by a biologic agent (e.g., pathogen (e.g., bacteria, virus, parasite, mold, etc.)), environmental agent or condition, or other exposure. In some embodiments, methods herein find use in the detection of necrosis and/or apoptosis for any desired purpose.

EXPERIMENTAL

Example 1

Quantitative Ex Vivo Gamma Counting Study

Experiments were conducted during development of embodiments herein to demonstrate that the uptake of $^{99m}$Tc-duramycin in susceptible tissues is significantly altered in response to the administration of chemotoxic drugs. This initial quantitative study was conducted by determining changes in radioactivity uptake in excised tissues using gamma counting ex vivo. Experiments were designed to survey changes in $^{99m}$Tc-duramycin uptake in tissues from treated versus untreated control groups after administration of a single dosage of each chemotherapeutic drug for each population of animals. Based on small-scale ex vivo multi-time point gamma counting studies, it was determined the window of peak signal intensity for most susceptible tissues for each chemotoxic drug. Accordingly, at designated time post-treatment, $^{99m}$Tc-duramycin was injected intravenously and each animal was euthanized for tissue collection and gamma counting. This is a standard practice in radionuclide studies that provides precise, quantitative biodistribution data for measuring changes in tracer uptake.

Figure 2:
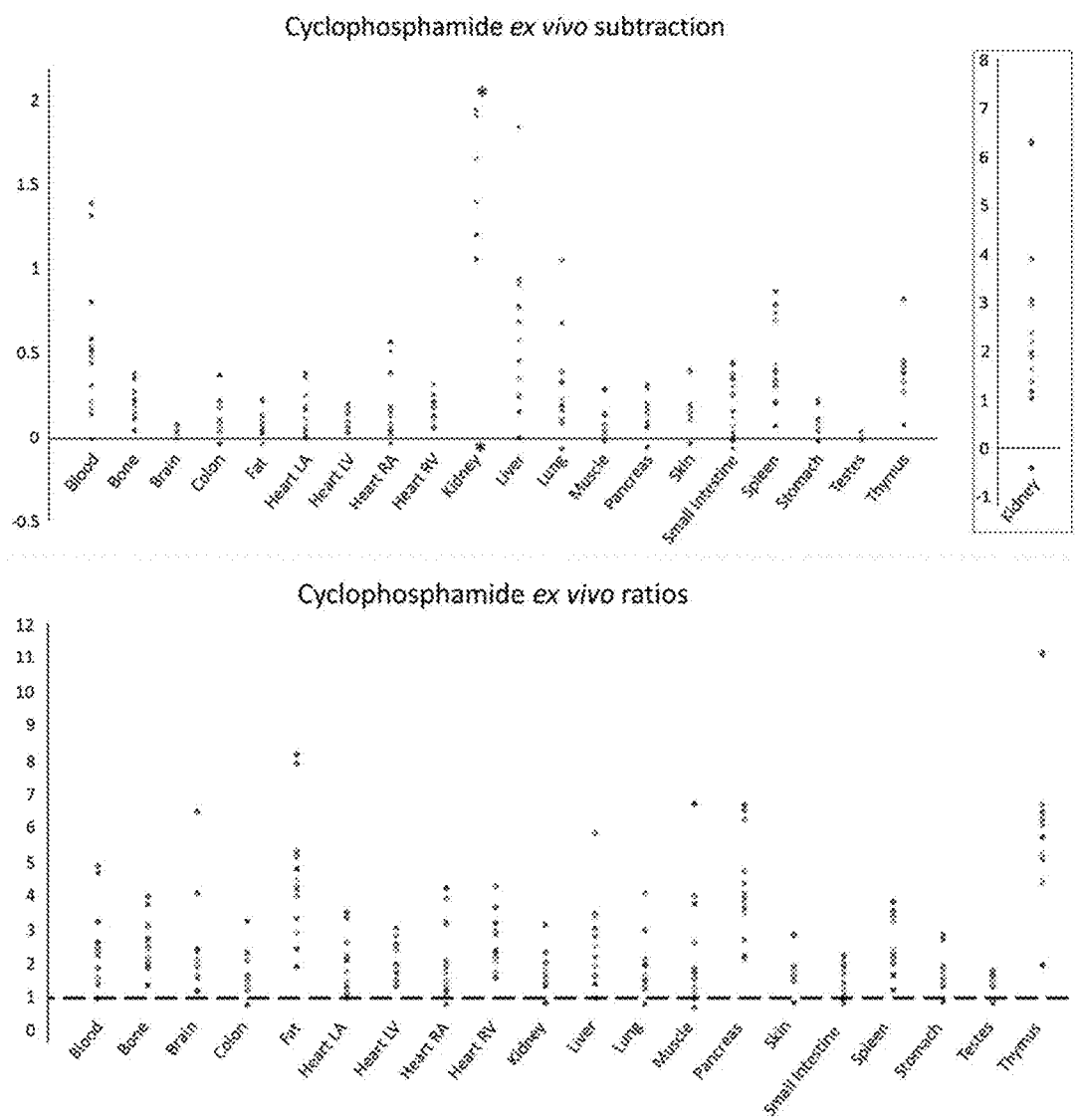
FIG. 2. ex vivo gamma counting results in cyclophosphamide treated rats.

The ex vivo gamma counting results are exemplified by FIG. 2, which demonstrates the changes in individual tissues at 2 days after the administration of a single dose of cyclophosphamide (80 mg/kg, i.p., n=15). The data can be expressed in two ways—net change in $^{99m}$Tc-duramycin uptake per unit tissue in cyclophosphamide-treated tissues relative to the mean value of the non-treated control population (FIG. 1A), and fold changes in $^{99m}$Tc-duramycin uptake over the mean of control (1B). The expression in the absolute change in $^{99m}$Tc-duramycin uptake weighed toward relatively high-count tissues, whereas the fold changes weighed toward relatively low-count tissues. A number of notable features are apparent. There was statistically significant elevation in $^{99m}$Tc-duramycin uptake in a wide range of tissues as a result of cyclophosphamide treatment. Tissues which had the largest elevation in $^{99m}$Tc-duramycin uptake were the kidneys, liver, spleen, thymus, lung, small intestine and bone. On the other hand, tissues with highest fold changes included the thymus, adipose tissue, pancreas, brain, right ventricle, liver and bone. A number of other tissues also exhibited statistically significant elevation in signal change albeit the changes were less drastic. The identity of tissues that exhibited greater changes was consistent with the known toxicity profile of cyclophosphamide. Visually, there appeared to be different levels of responses, where certain individuals responded more positively than others, and that the signal levels were heterogeneous from one individual to another. There were individual animals which exhibited relatively high signal changes systemically, suggesting a difference in susceptibility to drug toxicity on a personalized basis.

Experimental results from two other chemotherapeutics, methotrexate and cisplatin, provided additional support for the above findings. Methotrexate at a single dose of 100 mg/kg (n=15) resulted in notable elevation in $^{99m}$Tc-duramycin uptake in a number of tissues. Tissues with the highest increase in $^{99m}$Tc-duramycin uptake included the kidneys, small intestine, liver, and colon. According to fold chances, the most prominent tissues included the small intestine, colon, liver, thymus and kidneys. There were other lower uptake tissues which exhibited statistically significant elevation in signals. Overall, the changes in signals were consistent with the known toxicity effects of methotrexate including myelosuppression, cardiac toxicity, nephrotoxicity, adverse effect in the lung, digestive system and the immune system (spleen, bone marrow and thymus). Again, individuals that were more susceptible to methotrexate within the group, where the systemic uptake of $^{99m}$Tc-duramycin was significantly greater than the rest of the group.

Cisplatin is a platinum-based antineoplastic drug with known toxicity in a relatively broad range of organs and tissues. Cisplatin treatment in the rats (2 mg/kg, i.p., single dose, n=15) resulted in significantly elevated $^{99m}$Tc-duramycin uptake in a number of tissues in the body. The tissues which exhibited the greatest elevation in $^{99m}$Tc-duramycin uptake included the kidneys, small intestine, lung, right ventricle, stomach and skin. In comparison, tissues that experienced the highest fold changes included the adipose tissue, pancreas, kidneys thymus, stomach, small intestine. A number of remaining tissues also exhibited statistically significant signal changes albeit being relatively small. Susceptible tissues for cisplatin toxicity are known. Nephrotoxicity, for instance, is a major known side effect of cisplatin. Significant changes in the renal signals were consistent with cisplatin toxicity and demonstrated the feasibility of detection. An organ, such as the kidney, consists of different anatomical components (cortex, medulla, hilum), where the in vivo imaging data provide more spatial information by identifying signal changes within the substructures of an organ (see in vivo sections below).

The ex vivo gamma counting studies detected tangible and significant changes in the uptake of $^{99m}$Tc-duramycin among susceptible tissues in response to chemotherapeutic treatment. Data profiles of signal changes were consistent with observed toxicities of these test articles, and the responses were heterogeneous and individualized. The levels of $^{99m}$Tc-duramycin uptake are indicative that the approach may be sufficiently sensitive for detecting changes in response to drug toxicity at clinically relevant dosages. Although the ex vivo gamma counting is a standard practice in radionuclide studies, a notable limitation is that the tissue collection may be prone to sampling errors. In addition, this approach provides limited spatial information in terms of the distribution within an intact organ/tissue. Nevertheless, the ex vivo gamma counting confirms that signal changes in susceptible organs/tissues are significant and detectable in response to chemotoxic drug treatments, and captured the heterogeneous and individualized response to drug toxicity.

Example 2

Head-to-Head Comparison Study of Gamma Counting and In Vivo Data Acquisition

Experiments were conducted during development of embodiments herein to demonstrate that a whole-body in vivo imaging approach is capable of measuring relatively high-intensity as well as low, diffusive signals in an effective linear range. Experiments were conducted to examine the correlation between radioactivity counts obtained by gamma counting and by SPECT in the setting of in vivo imaging acquisitions.

A phantom study was performed involving serial dilution of an aliquot of known radioactivity and samples were imaged using the same acquisition parameters as for the in vivo rat study. From this titration it was determined that data correlated with theoretical values with an $R^2$ of 0.9986. The image acquisition has sufficient sensitivity with a linear range at a typical delivered dose of $^{99m}$Tc-duramycin. These data were indicative that the imaging technique is suitable for detecting signal changes in response to drug toxicity, including those at relatively low levels of uptake.

A head-to-head comparative study was conducted between ex vivo gamma counting and in vivo SPECT data. Rats were injected with $^{99m}$Tc-duramycin, and whole-body SPECT data were acquired at 1 hour. Each animal was immediately euthanized and the radioactivity in each organ and tissue was measured by ex vivo gamma counting. It was determined that the in vivo SPECT data correlated with results obtained from gamma counting ratiometrically with high $R^2$ values. Additionally when all data were expressed as % ID (percentage of injected dose) there was a strong linear correlation with a $R^2$ value of 0.9687.

Example 3

In Vivo Single Time Point Studies

A series of single time point in vivo imaging studies were performed to demonstrate that the changes in $^{99m}$Tc-duramycin uptake in tissues in response to chemotoxic drugs are significant and detectable noninvasively and systemically. The single time point studies were terminal so that they allowed immediate tissue retrieval for cross-validation using histopathological analyses. Based on small-scale ex vivo multi-time point gamma counting studies, it was determined the window of peak signal intensity for most susceptible tissues for each chemotoxic drug. Accordingly, the single time point in vivo imaging studies were carried out on day-2 after cyclophosphamide treatment (n=15), day-1 for methotrexate (n=15), and day-5 for cisplatin (n=15). Each animal was injected with about 2 mCi of $^{99m}$Tc-duramycin and after 1 hour the SPECT/CT/MRI data were acquired. From each group, the animals were immediately euthanized after imaging. The organs and tissues from three randomly selected individuals were collected, fixed and processed for histopathology.

Figure 3:
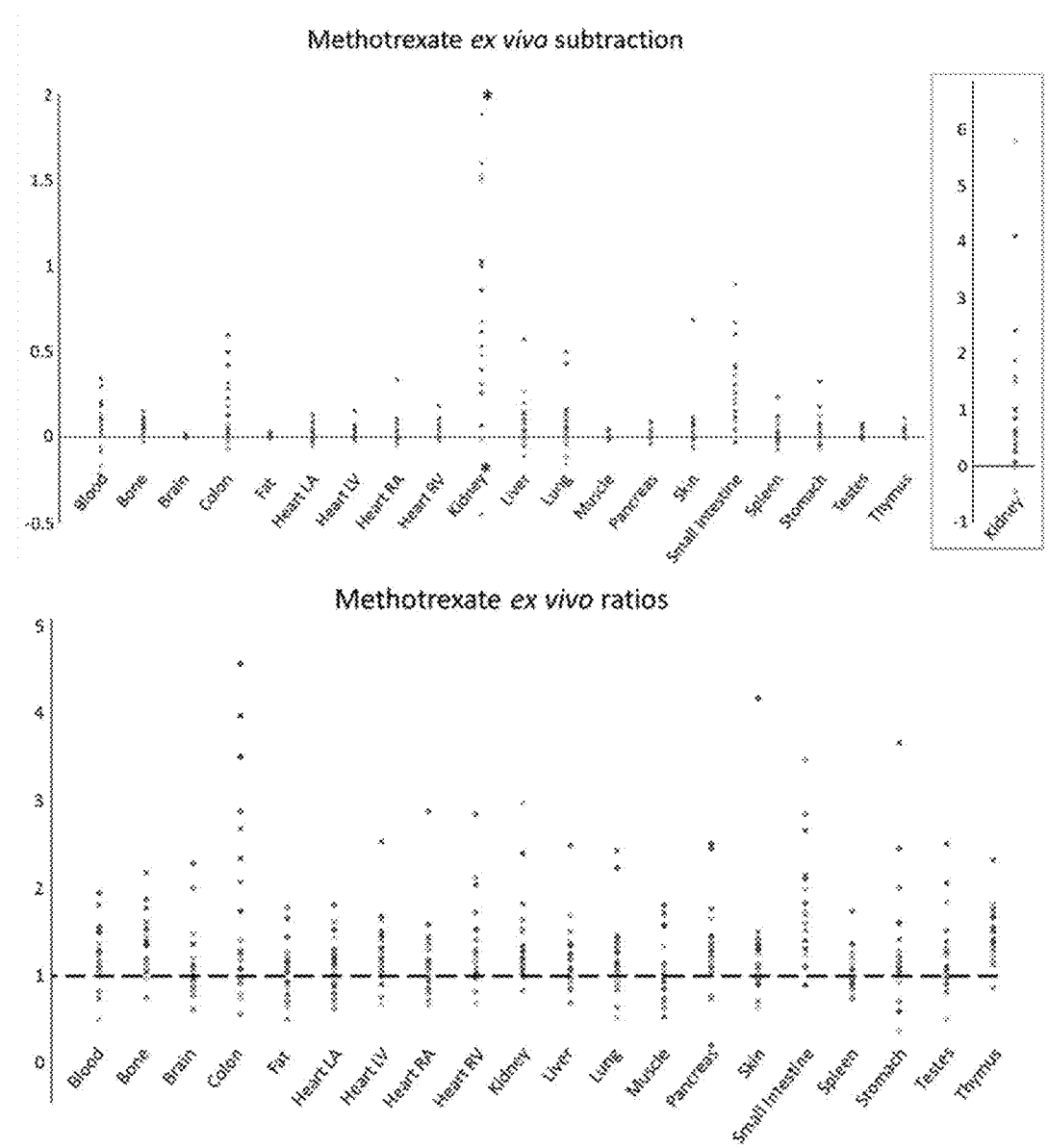
FIG. 3. ex vivo gamma counting results in methotrexate treated rats.

The cyclophosphamide in vivo data are shown in FIG. 3, which included net changes in $^{99m}$Tc-duramycin uptake in tissues relative to the mean values of non-treated controls. A single dose of cyclophosphamide caused widespread changes in $^{99m}$Tc-duramycin uptake, with key tissues including the kidneys—medulla and cortex, spleen, thymus and gut. A number of tissues also exhibited statistically elevated signals, albeit being relatively low, including the bones, adipose tissue, heart, lung, muscle, skin and stomach. The changes by the single time point in vivo imaging were positively associated with histopathological evidence. For instance, the in vivo thymus signal was accompanied by a significantly elevated apoptotic index. The presence of relatively high level of apoptotic nuclei was conspicuously seen in histology micrographs (FIG. 3). As a second example, the increased medulla signal in the kidneys was associated with significantly elevated apoptotic index in the local tissue—an unequivocal indication for nephrotoxicity. In a third instance, prominent in vivo signals were observed in bones, in particular at the epiphysis regions. These changes were confirmed in histopathology which showed extensive decellularization in the marrow.

Figure 4:
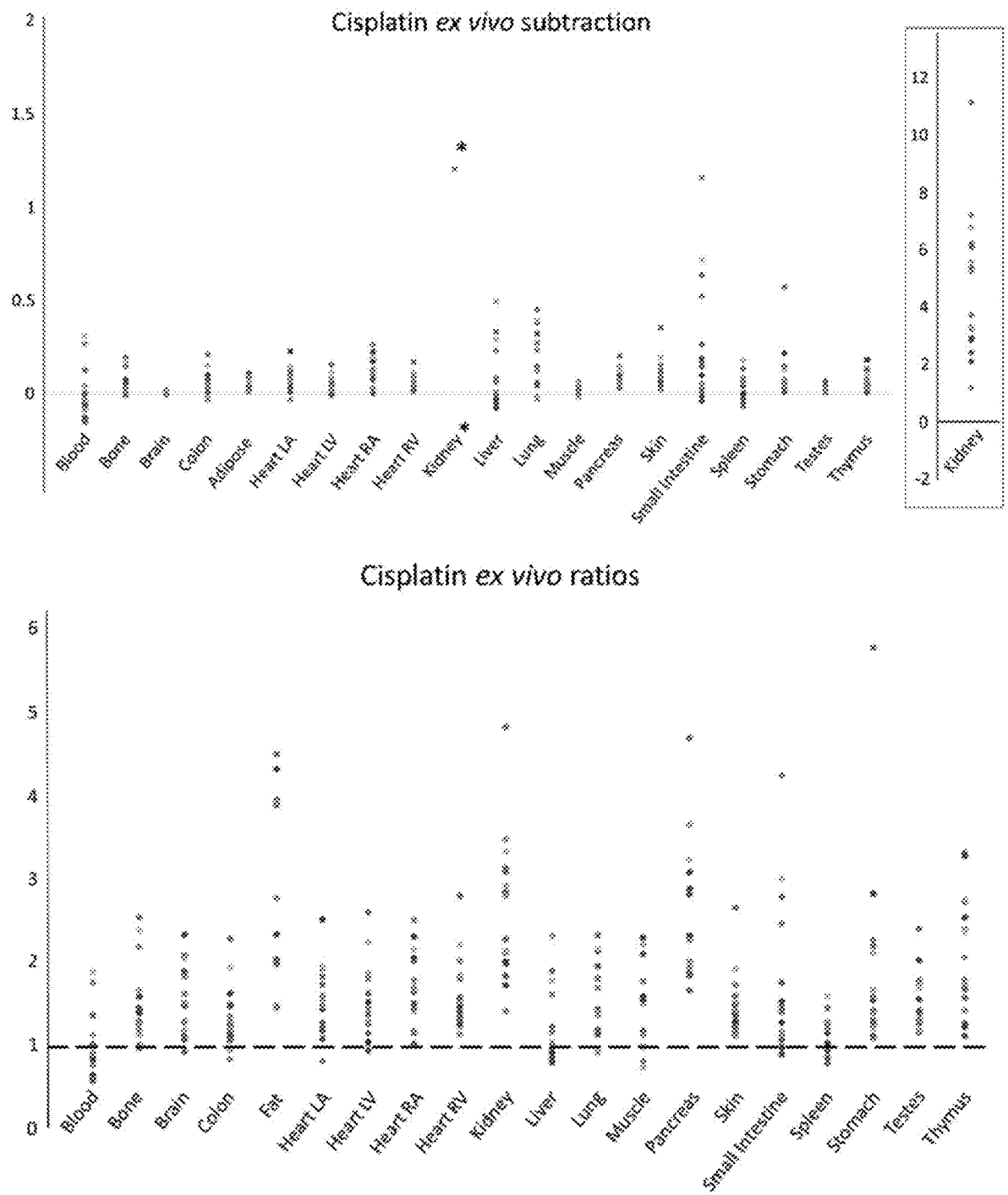
FIG. 4. ex vivo gamma counting results in cisplatin treated rats.

A second group of animals was with methotrexate as directed by the literature in an effort to examine whether early changes in toxicity would correlate with increases in $^{99m}$Tc-duramycin uptake. Tissues with the highest signal changes as net $^{99m}$Tc-duramycin uptake per unit tissue (FIG. 4) included the kidneys and colon. In terms of fold elevation, the tissues with highest changes included the colon, kidney—medulla, bone, spleen, and kidney—cortex. A number of lower uptake tissues also exhibited significantly elevated signals compared to the control group. When compared to the cyclophosphamide group, methotrexate treatment resulted in a different and more subtle toxicity profile. Among these changes, there were a number of notable features. First, changes in skin signals were non-uniform throughout the body. The ability to delineate such feature is critical to the detection of adverse toxicity effects without prior knowledge of susceptible regions within the same organ. This capability finds use in, for example, characterizing the toxicity profile of a drug and minimize sampling errors in histopathology-based toxicity studies. Second, the imaging approach identified drastically elevated signals in the joints (FIG. 4), which was consistent with the occurrence of joint necrosis reported in the literature. This was validated in histopathology, which revealed the presence of joint degeneration and thrombosis (FIG. 4).

Figure 5:
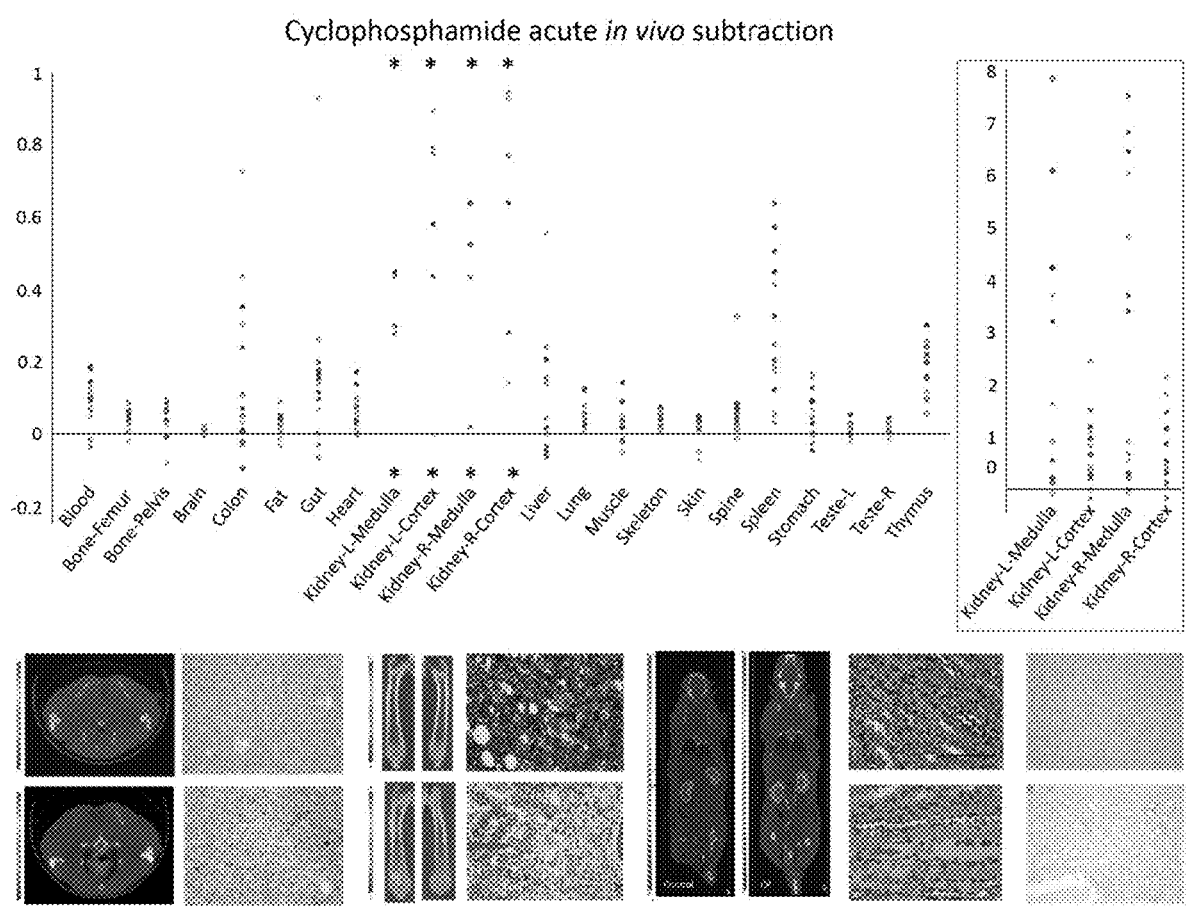
FIG. 5. In vivo single-time point study of cyclophosphamide treated rats.

A third group of animals (n=15) were treated with a single dose of cisplatin and were imaged at 5 days post-treatment. Increases in $^{99m}$Tc-duramycin uptake were observed in tissues known to be susceptible to cisplatin toxicity in a heterogeneous, individual-based manner. According to the net uptake of $^{99m}$Tc-duramycin (FIG. 5), the most prominent tissues included the kidneys, gut, spleen and skin. Tissues with the highest fold changes included the skin, kidneys, spleen, and gut. When compared to cyclophosphamide and methotrexate treated groups, cisplatin treatment resulted in a yet different toxicity profile. For instance, while cyclophosphamide toxicity appeared to primarily affect the infundibulum of the kidneys consistent with distal toxicity, cisplatin predominantly affected the parenchyma of the kidneys. Histopathology data demonstrated cellular degradation and significantly elevated apoptosis in the cortical region of cisplatin-treated animals. The imaging data clearly revealed increased signals in the marrow throughout the skeletal system (FIG. 5), including the femur, pelvic, and vertebra bodies. These changes were significant and systemic, consistent with the myelosuppression effect of cisplatin. The ability to noninvasively examine multiple locations will enable more objective conclusion on a test subject by minimizing sampling biases.

For the three tested drugs, the ex vivo biodistribution and in vivo imaging data were compared with standard serological toxicological panels in addition to histopathology analyses. No significant changes were observed in serological toxicological panels among the animals treated with the above chemotoxic drugs. The lack of significant serological changes indicated that the imaging approach has superior sensitivity, where the signal changes detected by imaging preceded functional deficiencies.

Example 4

In Vivo Dynamic Imaging Studies

In an effort to examine the spatial temporal dynamics of changes in imaging data over time and to further verify our initial observations, dynamic studies were performed after treatment with cyclophosphamide. Experiments were conducted during development of embodiments herein to demonstrate that the kinetics of drug toxicity-induced signal changes could be assessed noninvasively using dynamic whole-body imaging. This approach involved the acquisition of a baseline scan, prior to drug administration, followed by multiple post-treatment scans spanning the acute phase at 8, 48, 96, and 168 hours. The data set from each animal provided a wealth of information, which reflected the spatiotemporal distribution of tissue susceptibility to toxicity-induced injury. In addition, the baseline scan for each animal serves as an internal control. The repeated noninvasive imaging allowed continuous monitoring of tissue changes with individualized data analysis.

Figure 6:
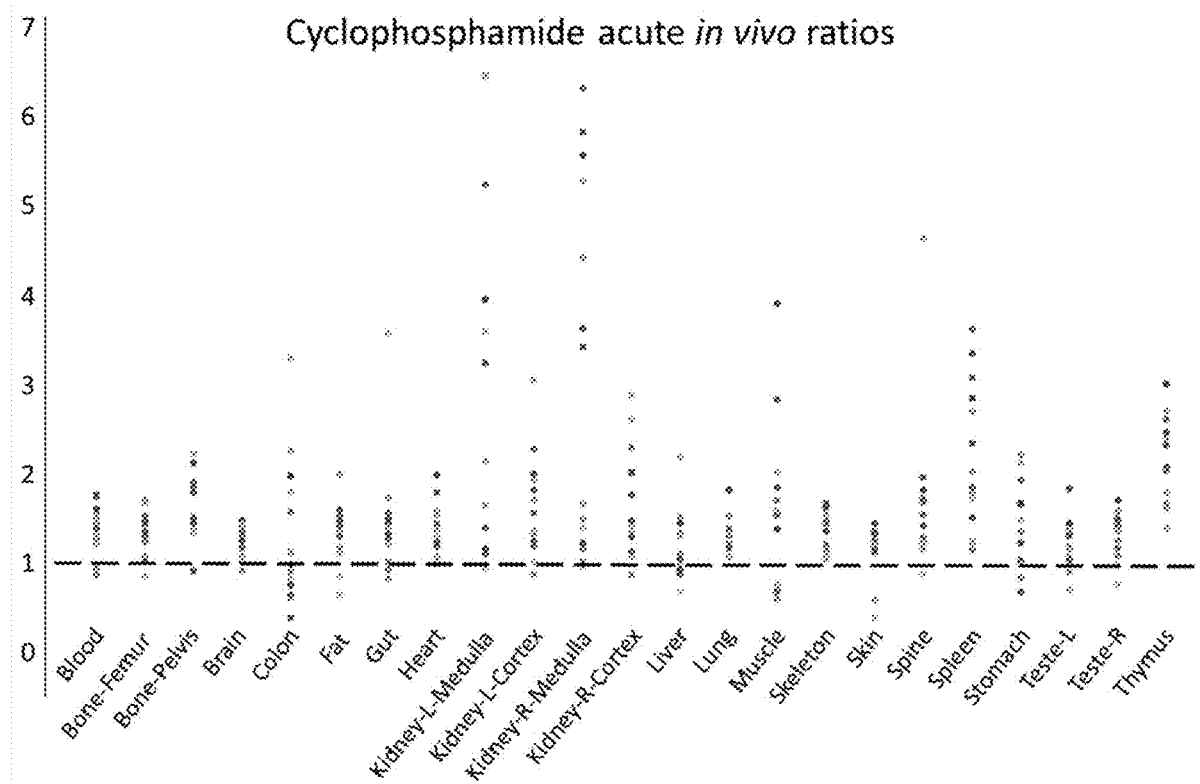
FIG. 6. Fold change data for in vivo single-time point cyclophosphamide treated rats.
Figure 7:
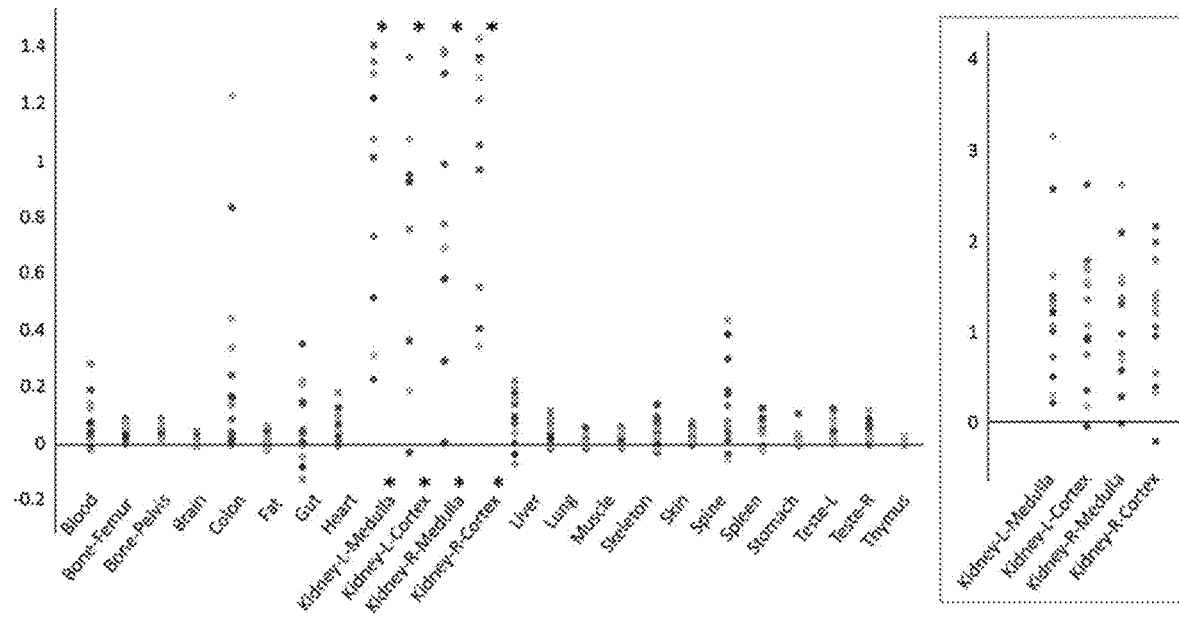
FIG. 7. In vivo single-time point study of methotrexate treated rats.
Figure 7:
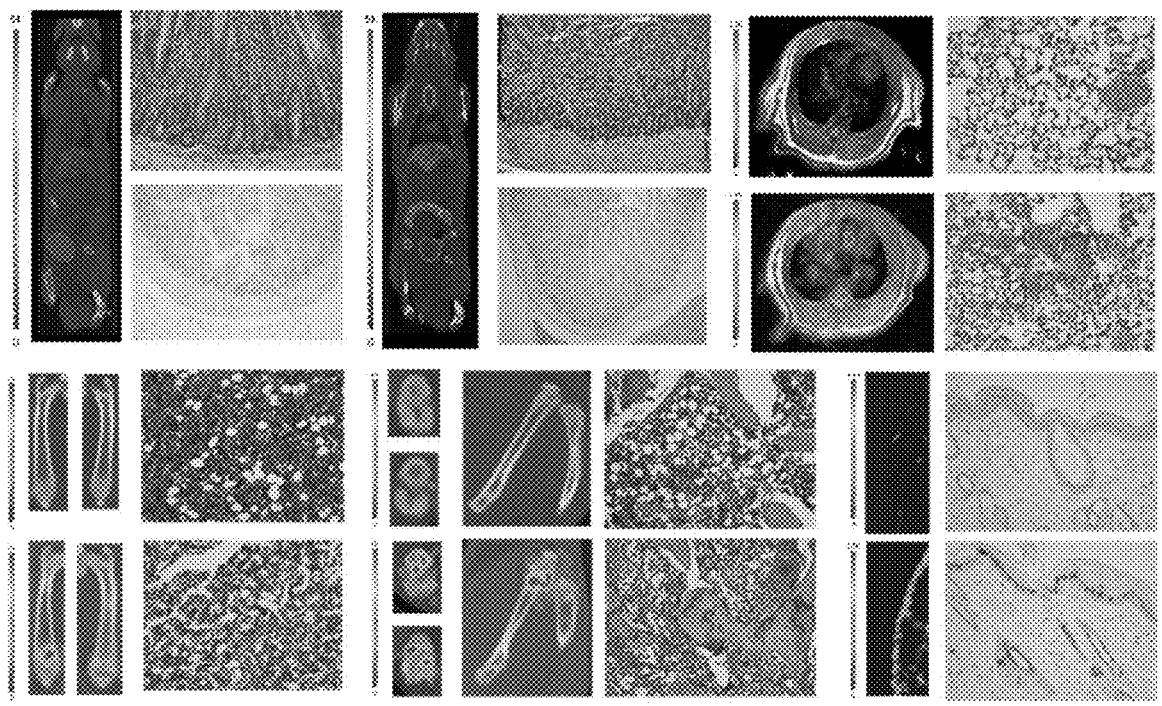
Figure 8:
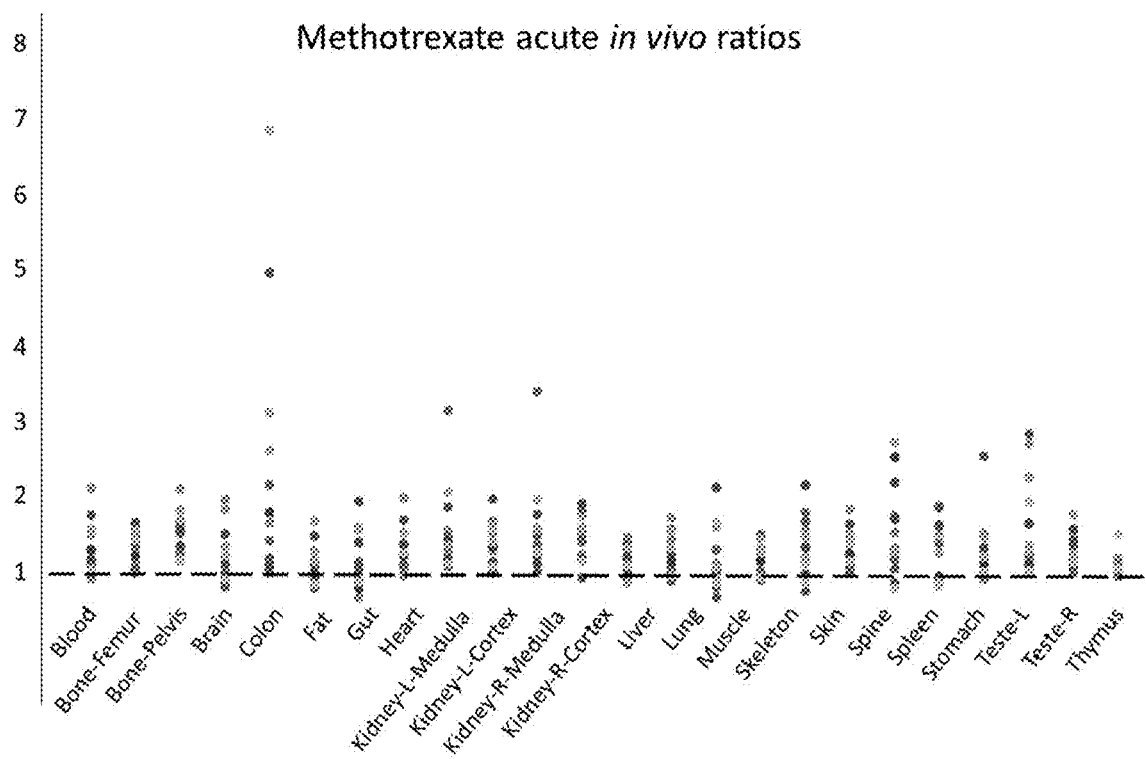
FIG. 8. Fold change data for in vivo single-time point methotrexate treated rats.
Figure 9:
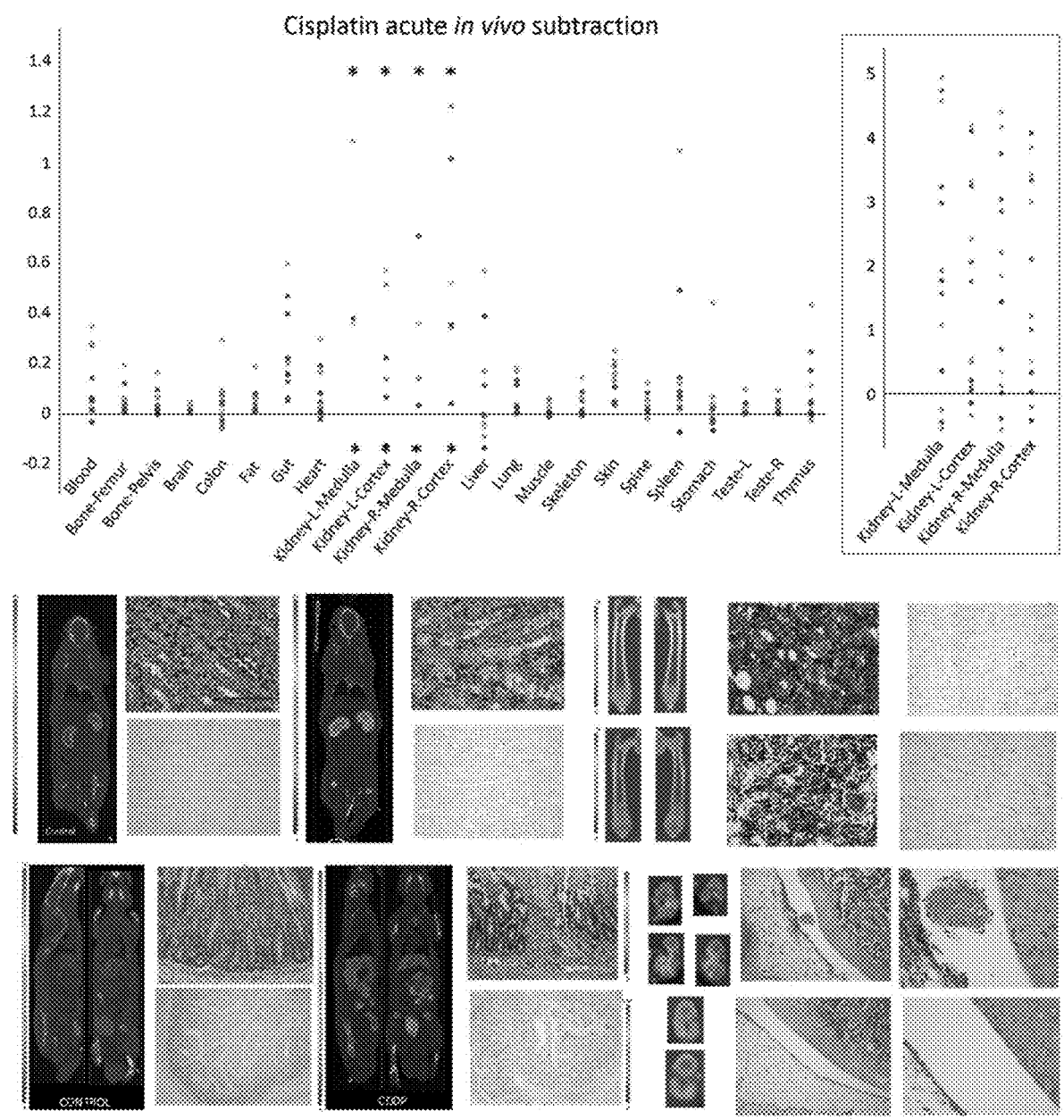
FIG. 9. In vivo single-time point study of cyclophosphamide treated rats.
Figure 10:
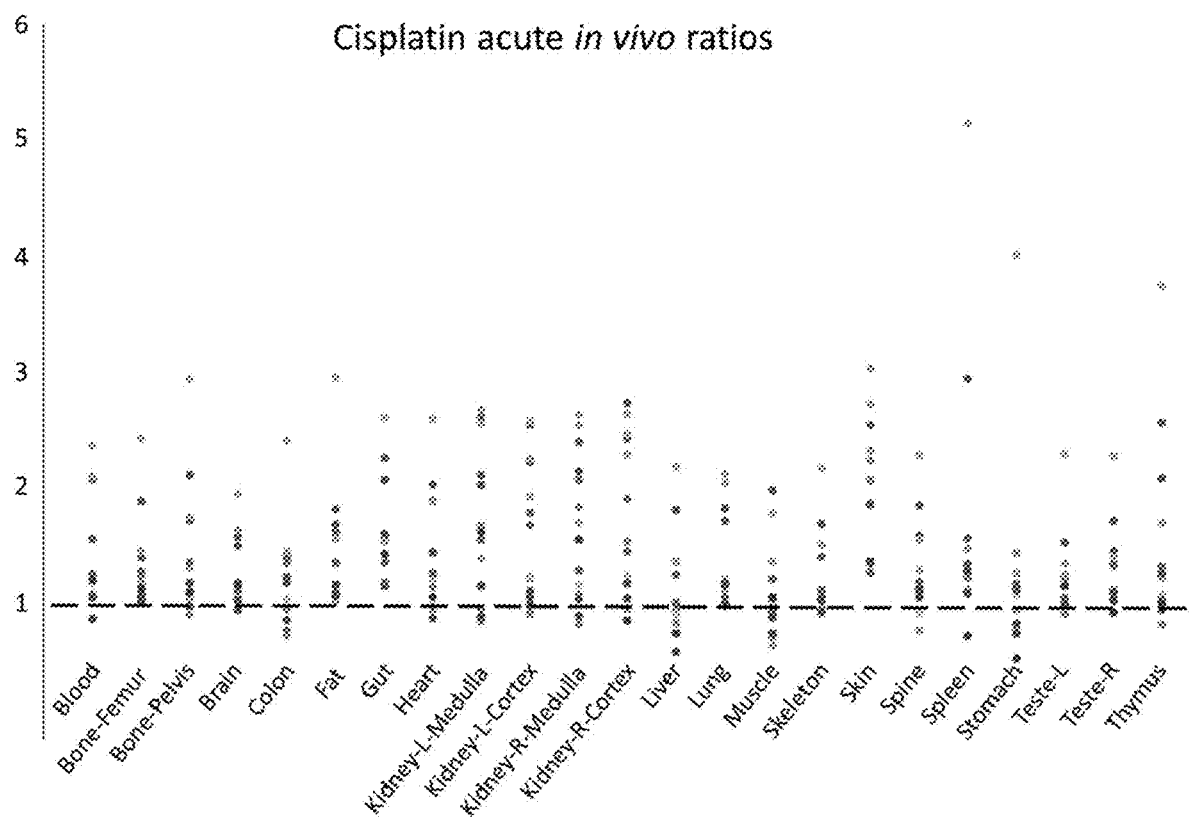
FIG. 10. Fold change data for in vivo single-time point cisplatin treated rats.
Figure 11:
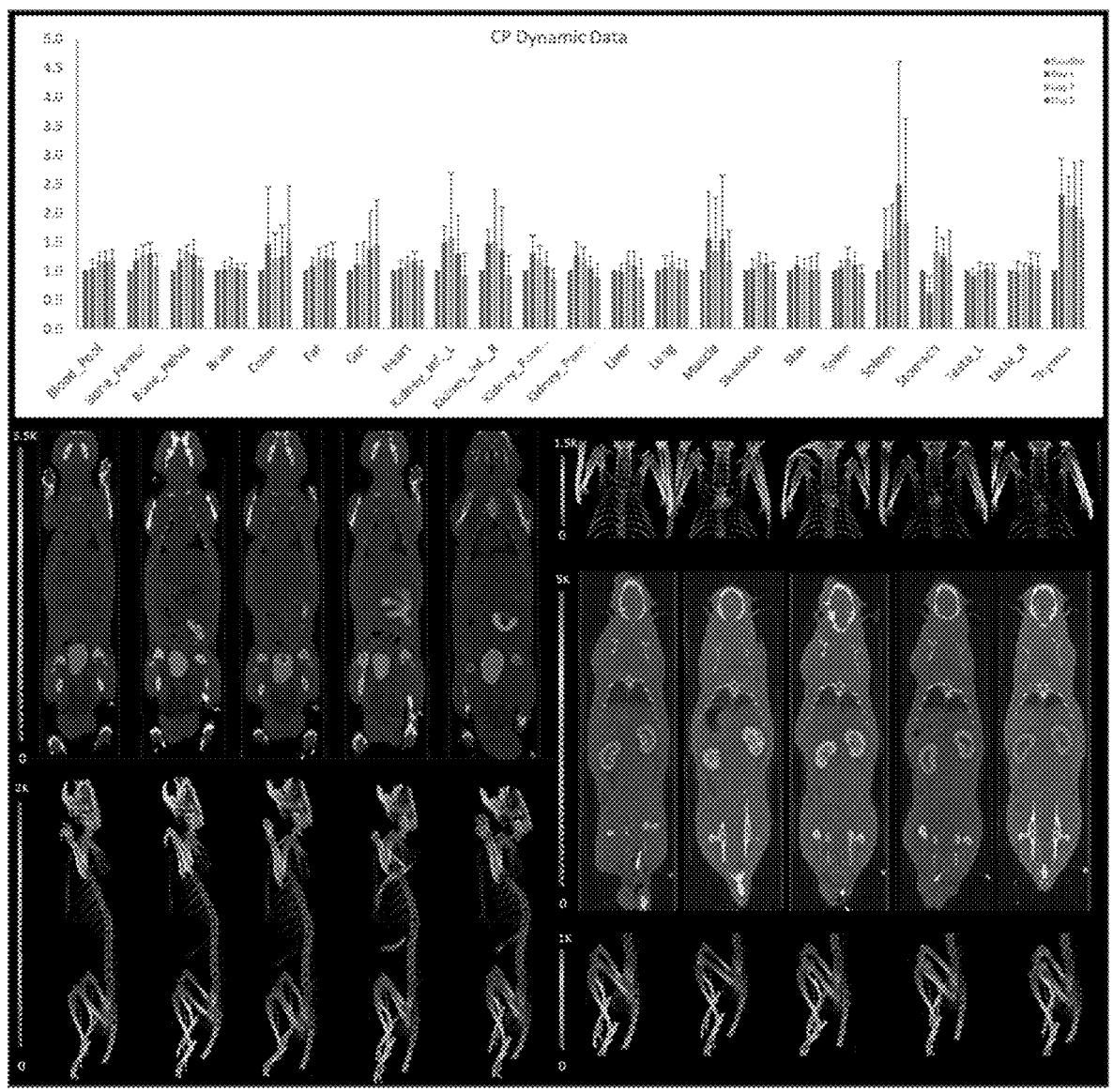
FIG. 11. In vivo dynamic study of cyclophosphamide treated rats.
Figure 12:
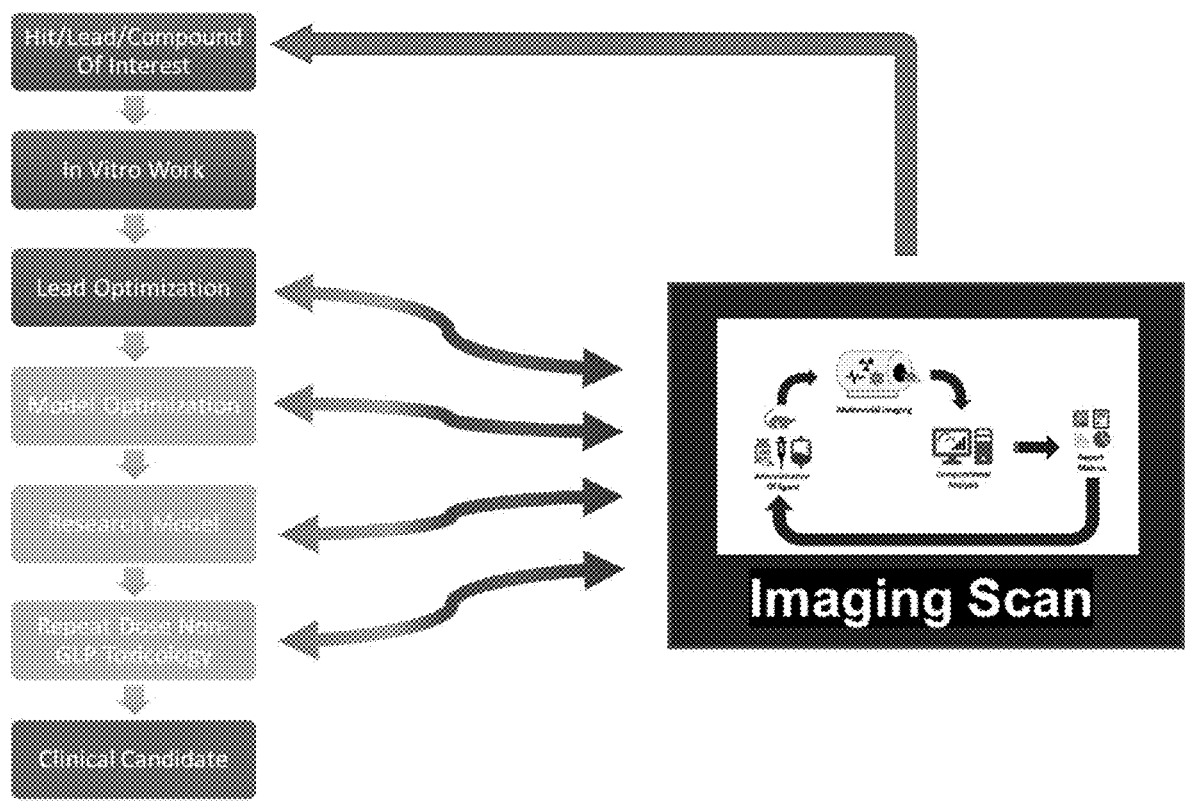
FIG. 12. Toxicity Scan as an approach in drug R&D.

A single dose of cyclophosphamide treatment resulted in widespread changes in $^{99m}$Tc-duramycin uptake throughout the body, where different tissues not only exhibited different levels of susceptibility, but also differed in the kinetics of signal changes. As shown in FIG. 7, among susceptible tissues, the colon, kidneys, skeletal muscles and thymus underwent early changes within 8 hours post-treatment, other tissues including the adipose tissue, bones, heart, liver, lung, small intestine, spleen and stomach had a delayed response with their signal changes peaked on or after day 3. The dynamics of signal changes in specific tissues when normalized to the baseline image could be seen visually as shown in FIG. 6. Compared to single time point studies, the dynamic imaging approach captured the presence and distribution of susceptible tissues by detecting the kinetics and trend of signal changes as a function of time.

Certain tissues exhibited greater coefficients of variation over time, when the dynamic data for each individual was normalized to its own baseline. Tissues with elevated coefficients of variation compared to the baseline included the bone, colon, gut, heart, skin, and thymus. A greater coefficient of variation is indicative of a wider range of susceptibility in response to the same drug treatment from one individual to another.

The invention claimed is:

1. A method of detecting toxicity-induced injury through generating a whole body visual map of systemic toxicity-induced injury in intact organs and tissues of a subject by whole body in vivo imaging, the method comprising:
    (a) administering to the subject for a period of time a toxicity-inducing chemical, followed by administering a molecular imaging agent to the subject, wherein the molecular imaging agent comprises a detectable moiety selected from technetium-99m ($^{99m}$Tc), gallium-67 ($^{67}$Ga), yttrium-91 ($^{91}$Y), indium-111 ($^{111}$In), rhenium-186 ($^{186}$Re), thallium-201 ($^{201}$Tl), gadolinium(III), iron oxide, iron platinum, or manganese directly bound to a binding moiety specific for an externalized phospholipid selected from duramycin, duramycin B, duramycin C, cinnamycin, or a PE-binding portion thereof;
    (b) performing molecular imaging scans at multiple time points of the subject;
    (c) detecting the molecular imaging agent within the subject dynamically by determination of changes in signal intensity, spatiotemporal occurrence of signal distribution or signal changes over time, wherein the combination of the agent and the scanning methods minimizes systemic background, improves target-to-background ratio so that high-intensity as well as low diffusive signals are dynamically detected over an effective linear range, wherein statistically elevated signals are identified in bones, adipose tissue, heart, lung, muscle, skeletal muscles, skin, stomach, colon, kidneys, thymus, liver, spleen, or small intestine tissues, wherein the signals may appear within eight hours post-treatment or may peak on or after day three post-treatment, and wherein the measured signal changes create a systemic whole-body visual toxicity profile thereby mapping toxicity-induced injury of the toxicity-inducing chemical.

2. The method of claim 1, wherein the molecular imaging scan comprises a technique selected from Magnetic Resonance Imaging (MM), planar scintigraphy (PS), Positron Emission Tomography (PET), Single Photon Emission Computed Tomography (SPECT), and Computed Tomography (CT).

3. The method of claim 1, wherein the toxicity-inducing chemical is- a chemotherapeutic or other drug that may cause a toxicity-induced tissue injury.

* * * * *

UNITED STATES PATENT AND TRADEMARK OFFICE
CERTIFICATE OF CORRECTION

| | |
|---|---|
| PATENT NO. | : 11,607,462 B2 |
| APPLICATION NO. | : 15/981568 |
| DATED | : March 21, 2023 |
| INVENTOR(S) | : Ming Zhao and Steven E. Johnson |

It is certified that error appears in the above-identified patent and that said Letters Patent is hereby corrected as shown below:

In the Specification

On Column 1, Line 11, please include the following paragraph under the CROSS-REFERENCE TO RELATED APPLICATION paragraph:
-- GOVERNMENT LICENSE RIGHTS
This invention was made with government support under grant number R01 CA185214 awarded by the National Institutes of Health. The government has certain rights in the invention. --

Signed and Sealed this
Twenty-first Day of November, 2023

Katherine Kelly Vidal
*Director of the United States Patent and Trademark Office*